United States Patent
Moshyedi

[11] Patent Number: 5,770,215
[45] Date of Patent: Jun. 23, 1998

[54] MULTIVITAMIN/VASCULAR OCCLUSION INHIBITING COMPOSITION

[76] Inventor: Emil Payman Moshyedi, 49 Rutland Rd., West Babylon, N.Y. 11704

[21] Appl. No.: 778,758

[22] Filed: Jan. 6, 1997

[51] Int. Cl.[6] .................................................. A61K 31/00
[52] U.S. Cl. .......................................... 424/440; 424/451
[58] Field of Search ................... 424/440, 450, 424/451; 549/315, 408; 568/182

[56] References Cited

U.S. PATENT DOCUMENTS

| | | | |
|---|---|---|---|
| 4,491,574 | 1/1985 | Seifter et al. | 424/10 |
| 4,725,427 | 2/1988 | Ashmead | 424/44 |
| 5,393,531 | 2/1995 | Gerhard et al. | 424/466 |
| 5,401,730 | 3/1995 | Sauvage et al. | 514/165 |
| 5,443,850 | 8/1995 | Thys-Jacobs | 424/682 |
| 5,494,668 | 2/1996 | Patwardhan | 424/195.1 |
| 5,505,961 | 4/1996 | Shelley et al. | 424/451 |

*Primary Examiner*—Thurman K. Page
*Assistant Examiner*—D. Faulkner
*Attorney, Agent, or Firm*—Michael I. Kroll

[57] ABSTRACT

The present invention relates to a vitamin supplement containing from 5% to 1000% of the RDA of vitamins and a therapeutically effective amount of a vascular occlusion inhibiting compound which is preferably aspirin (acetylsalicylic acid). The vitamins are selected from vitamins A, D; E, K, C, thiamin, riboflavin, niacin, niacinamide, $B_6$, folate, $B_{12}$, biotin, pantothenic acid and mixtures thereof. The composition can be in capsule or tablet form, may further contain minerals, herbal extracts, homeopathics or other therapeutic substances, and finds particular utility with regard to cardiac care patients.

5 Claims, 3 Drawing Sheets

Acetylsalicylic Acid    18
(Aspirin)    20

Fat-Soluble Vitamins

<u>38</u> A (Retinoids; β-carotene)

<u>40</u> D (a mixture of sterols, including Ergocalciferol ($D_2$) and Cholecalciferol ($D_3$))

<u>42</u> E (Tocopherols and tocotrienols)

<u>44</u> K (compounds with phylloquinone activity)

32

Water-Soluble Vitamins

<u>46</u> C (Ascorbic Acid)

<u>48</u> $B_1$ (Thiamin)

<u>50</u> $B_2$ (Riboflavin)

<u>52</u> $B_6$ (Pyridoxine, Pyridoxal, Pyridoxamine)

<u>54</u> $B_{12}$ (Cyanocobalamin)

<u>56</u> Niacinamide (Nicotinamide), Niacin (Nicotinic Acid)

<u>58</u> Pantothenic Acid

<u>60</u> Biotin

<u>62</u> Folic Acid (Folate)

34

Minerals/Trace Elements

| | |
|---|---|
| <u>64</u> Selenium | <u>84</u> Phosphorus |
| <u>66</u> Zinc | <u>86</u> Iodine |
| <u>68</u> Magnesium | <u>88</u> Potassium |
| <u>70</u> Calcium | <u>90</u> Molybdenum |
| <u>72</u> Iron | <u>92</u> Vanadium |
| <u>74</u> Manganese | <u>94</u> Fluoride |
| <u>76</u> Copper | <u>96</u> Chloride |
| <u>78</u> Chromium | <u>98</u> Nickel |
| <u>80</u> Cobalt | <u>100</u> Tin |
| <u>82</u> Boron | <u>102</u> Silicon |

MULTIVITAMIN/VASCULAR OCCLUSION INHIBITING COMPOSITION

BRIEF SUMMARY OF THE INVENTION

BACKGROUND OF THE INVENTION

1. Field of the Invention

The instant invention relates generally to compositions for inhibiting vascular occlusion in humans and more specifically to compositions for inhibiting vascular occlusion which further contain nutritional supplements.

2. Description of the Prior Art

Compositions for inhibiting platelet aggregation are known in the art. For example, U.S. Pat. No. 5,401,730 (Sauvage, L.R. et al., 28 Mar. 1995) discloses a method of treating a patient comprising the administration of a combination of acetylsalicylic acid (aspirin), citric acid and thiamine, optionally in further combination with zinc.

U.S. Pat. No. 4,491,574 (Seifter, E., 1 Jan. 1985) discloses a therapeutic composition comprising aspirin in combination with vitamin A or a precursor of vitamin A to reduce toxicity and ulcerogenesis.

SUMMARY OF THE INVENTION

The present invention is concerned with a composition for inhibiting vascular occlusion in humans and more specifically to compositions for inhibiting vascular occlusion which further contain nutritional supplements.

A primary object of the present invention is to provide a single composition which contains both vitamins and a vascular occlusion inhibitor.

Another object of the present invention is to provide a vitamin supplement in combination with aspirin (acetylsalicylic acid).

An additional object of the present invention is to provide a vitamin supplement in combination with aspirin (acetylsalicylic acid) and nutritional minerals.

Another object of the present invention is to provide a vitamin supplement/vascular occlusion inhibitor which simplifies the process of treating cardiac care patients by combining aspirin and vitamins into a single formulation.

A further object of the present invention is to provide a vitamin supplement in combination with aspirin (acetylsalicylic acid) and one or more of herbal extracts, homeopathic compositions, red wine concentrates and amino acid supplements.

A further object of the present invention is to provide a method of treating a cardiac care patient by administering to the patient a vitamin supplement containing a vascular occlusion inhibitor such as aspirin.

Yet another object of the present invention is to provide a composition for reducing inflammation while providing nutritional supplements.

Another object of the present invention is to provide a composition for reducing fevers while providing nutritional supplements.

Yet another object of the present invention is to provide a composition for ameliorating pain while providing nutritional supplements.

Yet another object of the present invention is to provide a vitamin/mineral supplement in combination with aspirin for treating high risk pregnancies, with the aspirin useful for reducing the danger of eclampsia and pre-eclampsia.

Yet another object of the present invention is to provide a vitamin/mineral supplement in combination with aspirin, with the aspirin useful for reducing the danger of colorectal cancer.

A further object of the present invention is to provide a vitamin/mineral supplement in combination with aspirin for the combined effect of reducing fever, inflammation and/or pain while providing nutritional supplementation.

Another object of the present invention is to provide a vitamin/mineral supplement in combination with aspirin, with the aspirin useful for reducing the spread of viruses.

A further object of the present invention is to provide a vitamin/mineral supplement in combination with aspirin, with the aspirin useful for reducing heart attack damage, improving heart attack survival, reducing the incidence of second heart attacks and/or reducing death secondary to heart attacks.

Another object of the present invention is to provide a vitamin/mineral supplement in combination with aspirin, with the aspirin useful for reducing or preventing strokes and/or transient ischemic attacks.

A further object of the present invention is to provide a vitamin/mineral supplement in combination with aspirin, with the aspirin useful for reducing the likelihood and/or severity of migraine attacks.

Another object of the present invention is to provide a vitamin/mineral supplement in combination with aspirin, with the aspirin useful for reducing or preventing vascular dementia.

Yet another object of the present invention is to provide a vitamin/mineral supplement in combination with aspirin, with the aspirin useful for reducing the risk of cataract formation.

The foregoing and other objects, advantages and characterizing features will become apparent from the following description of certain illustrative embodiments of the invention.

The novel features which are considered characteristic for the invention are set forth in the appended claims. The invention itself, however, both as to its construction and its method of operation, together with additional objects and advantages thereof, will be best understood from the following description of the specific embodiments when read and understood in connection with the accompanying drawings. Attention is called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views.

FIG. 3 is a chart illustrating various vitamins and minerals which can be effectively included in the composition of the present invention.

Figure 1:
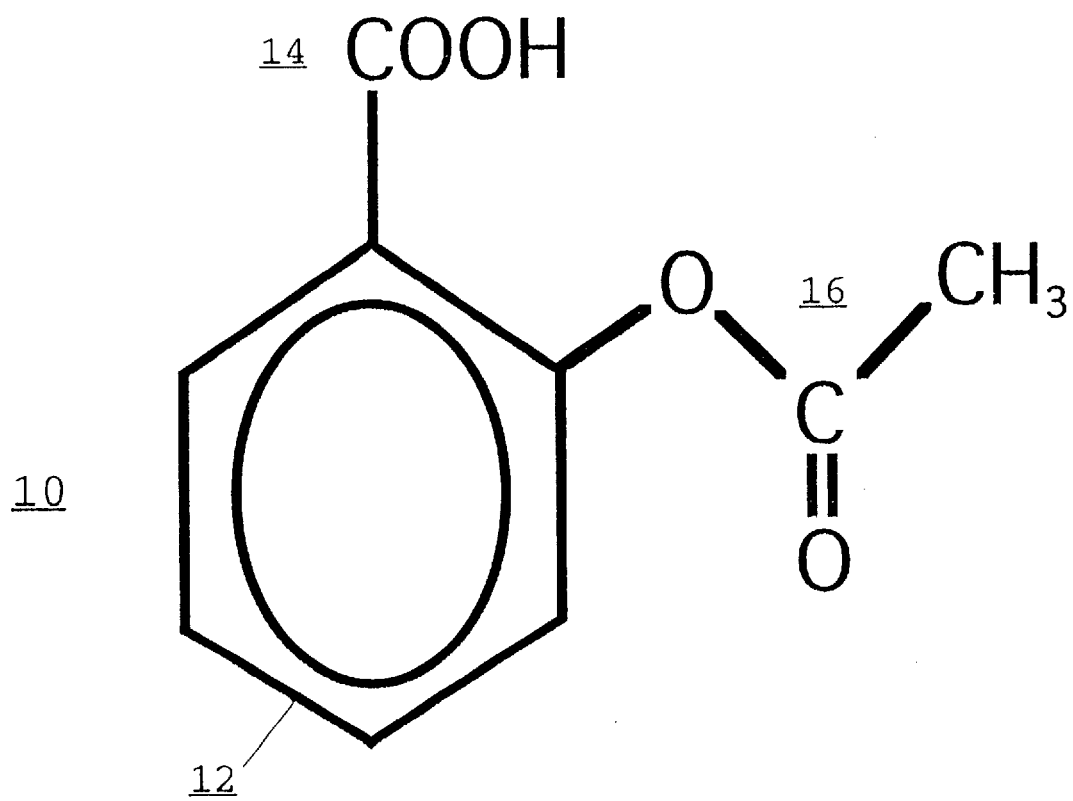
FIG. 1 is the chemical structure for acetylsalicylic acid, also known as aspirin, the preferred vascular occlusion inhibitor in the composition of the present invention.

LIST OF REFERENCE NUMERALS USED IN THE DRAWING FIGURES the chemical structure for acetylsalicylic acid (aspirin)

the phenyl ring which is the primary chemical moiety in acetylsalicylic acid 10 the carboxyl group attached to the phenyl group 12 the acetoxy group attached to the phenyl group 12, in the position ortho- to the carboxyl group 10 acetylsalicylic acid, the IUPAC name for aspirin 20 aspirin, the generic name for acetylsalicylic acid 18 a cardio/cerebrovascular patient care composition, the preferred utility for the compositions of the present invention aspirin, the first major active component of the composition of the present invention a plurality of vitamins, the second major active component of the composition of the present invention one or more nutritional minerals, an optional minor component of the composition of the present invention binder for holding the various components 24, 26, 28 together fat-soluble vitamins which may be effectively employed in the compositions of the present invention water-soluble vitamins which may be effectively employed in the compositions of the present invention nutritional minerals which may be effectively employed in the compositions of the present invention Vitamin A, including the retinoids and β-carotene Vitamin D, actually a mixture of various sterols including ergocalciferol (vitamin $D_2$) and cholecalciferol (Vitamin $D_3$)

Vitamin E, a mixture of various tocopherols and tocotrienols, of which d-α-tocopherol preferred Vitamin K, including all compounds which exhibit a biological activity similar to that of phylloquinone Vitamin C, also known as ascorbic acid Vitamin $B_1$, also known as thiamin Vitamin $B_2$, also known as riboflavin Vitamin $B_6$, the generic name for pyridoxine, its amine (pyridoxamine) and its aldehyde (pyridoxal)

Vitamin $B_{12}$, also known as cyanocobalamin niacin, the USP name for nicotinic acid, and its amide niacinamide (nicotinamide)

pantothenic acid biotin folic acid, also known as pteroylglutamic acid, or folate selenium, an essential nonmetal mineral zinc, an essential metal mineral magnesium calcium, an essential nonmetal mineral iron, an essential metal mineral manganese, a trace metal mineral copper chromium cobalt boron phosphorus iodine potassium molybdenum vanadium fluoride chloride nickel tin silicon

DETAILED DESCRIPTION OF THE PREFERRED EMBODIMENTS

Turning now descriptively to the drawings, in which similar reference characters denote similar elements throughout the several views, the Figures illustrate a vitamin supplement of the present invention.

With reference to FIG. 1, the preferred vascular occlusion inhibitor is aspirin (acetylsalicylic acid). The chemical structure of aspirin consists of a phenyl ring 12 substituted with a carboxyl group 14 and an acetoxy group 16, positioned ortho- to each other.

Figure 2:
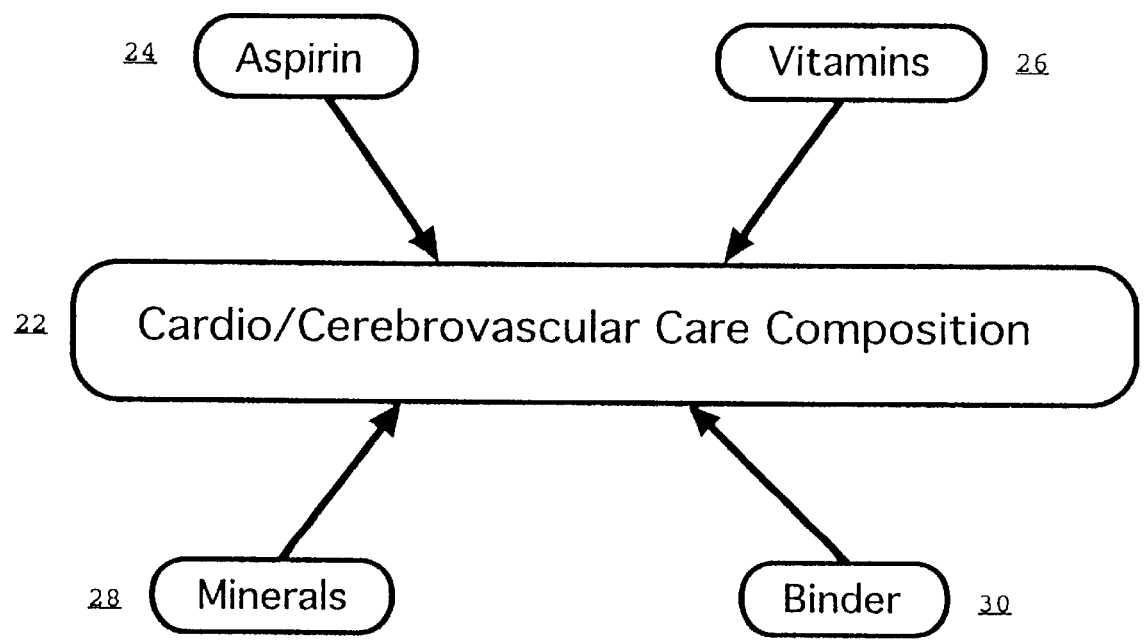
FIG. 2 is a diagrammatic view of various components which may find use in the present invention.

FIG. 2 illustrates, in general terms, various components which may be used in the compositions of the present invention, in this case illustrated as the specific embodiment of a cardio/cerebrovascular care composition 22. The composition contains the necessary components, vitamins 26 and a vascular occlusion inhibitor, in this case aspirin 24. Optional components include minerals 28 and binders 30, for example, when tablet form is desired.

FIG. 3 illustrates the various vitamins and minerals which can be effectively included in the compositions of invention. The vitamins can be divided into two broad groups, the fat-soluble 32 and the water-soluble 34 vitamins. Of the vitamins, vitamins A 38, D 40, E 42 and C 46 are preferred. Optionally, the composition can contain one or more minerals 36. Of the minerals, selenium 64, zinc 66, magnesium 68, calcium 70, iron 72, manganese 74, copper 76, chromium 78, potassium 88, nickel 98 and tin 100 are preferred, with selenium 64, zinc 66 and magnesium 68 most preferred. The compositions of the present invention are intended to include, without limitation, combinations of aspirin and vitamin(s), aspirin and mineral(s), and aspirin, vitamin(s) and mineral(s). As long as the composition contains at least one mineral or vitamin, all combinations of vitamins and/or minerals are within the scope of the present invention.

Platelet aggregation has been implicated in the process of thrombus formation, a contributor to vascular obstruction in humans. Thrombus formation involves a complex interaction of aggregated platelets and activated coagulation factors with a damaged vessel wall. Circulating platelets are normally nonadherent to endothelium or to each other, but when the endothelial lining of a vessel is damaged, the platelets adhere to exposed subendothelial collagen. This is the first step in the formation of hemostatic plugs, and requires participation of a protein made by endothelial cells called the von Willebrand factor (vWF). The vWF is found both in the vessel wall and in plasma, and binds during platelet adhesion to a receptor present on a glycoprotein of the platelet surface membrane.

Next, platelets are activated in reactions initiated by collagen and by thrombin formed at the injury site. These stimuli activate phospholipase C, an enzyme that hydrolyzes the membrane phospholipid, phosphatidyl inositol triphosphate. Products of this reaction activate protein kinase C and also increase the calcium concentration of platelet cytosol. As a result, a series of progressive, overlapping events ensue. The platelets change shape and develop long pseudopods. A receptor is assembled on the platelet surface membrane, and fibrinogen and other adhesive proteins bind to this receptor causing platelets to stick to each other. Arachidonic acid is liberated from membrane phospholipids and undergoes oxidation to products that include prostaglandin $H_2$ ($PGH_2$), which serves as an important cofactor for collagen-induced platelet activation, and thromboxane $A_2$ ($TxA_2$), which can act itself as as an additional platelet activator. The contents of platelets are secreted, including adenosine diphosphate (ADP) which can also stimulate platelet activation and recruit new platelets into the growing hemostatic plug.

After platelet aggregation, fibrinogen in the circulating blood is converted to fibrin to physically tie the hemostatic platelet plug in place. The platelet surface undergoes a reorganization that exposes procoagulant phospholipids needed for enzyme/cofactor complexes of blood coagulation to form on the platelet surface. Secretion of platelet factor V from platelet s-granules provides a key component for one of the enzyme/cofactor complexes. As a result, thrombin is generated in increasing amounts on the platelet surface, and converts fibrinogen into fibrin with the formation of fibrin strands that radiate outward from aggregated platelets helping to secure the platelet plug to the site of injury. Additionally, a mechanism within the platelets is activated which results in contraction of platelet actinomycin. This compresses and consolidates the platelet plug, further securing it to the site of injury.

In the in vivo regulation of thrombus formation, platelet aggregation is mediated by the $PGH_2$ derivative prostacyclin ($PGI_2$). Prostacyclin is also a vasodilator and is believed to render the vessel lining inert to platelet interactions. Thus, $TxA_2$ and $PGI_2$ have opposing physiological effects on platelet aggregation as well as on vascular caliber ($TxA_2$ induces vascular constriction while $PGI_2$ induces vascular dilation), and the degree of the physiological effect of each in the cardiovascular system on the regulation of thrombus formation and vascular caliber is determined primarily by their relative concentrations.

Accordingly, inhibition of platelet aggregation and vascular occlusion is a primary concern in cardiac and cerebrovascular care patients, both for treatment of, and prophylaxis of, thrombosis and vascular spasm. Cardiac care patients include, for example, potential and prior heart attack patients and potential and prior stroke patients. The most widely accepted substance for this purpose is aspirin (acetylsalicylic acid). In the arachidonic acid cascade, aspirin acts as a cyclooxygenase inhibitor, blocking the conversion of arachidonic acid to the $PGH_2$ precursor prostaglandin $G_2$ ($PGG_2$). Since $PGG_2$ is a precursor to both $TxA_2$ and $PGI_2$, aspirin blocks both the aggregation inducing and aggregation inhibiting effects of these factors, respectively.

With regard to the amount of aspirin in the compositions of the inventions, a therapeutically effective and nontoxic amount can be readily determined by the ordinary skilled physician, with the precise amount depending on various factors, including, for example, size and health of the patient. Generally accepted values include from 0.5 mg of aspirin per Kg of body weight of the patient per day to 5 or more mg/Kg/a range most people, a range of from about 10 to about 1000 mg/day, and preferably from about 25 to about 500 mg/day, will often be appropriate, particularly in the range of from about 100 to about 250 mg/day. It is anticipated that the above-described aspirin concentrations will be most appropriate for use in compositions for treating cardio/cerebrovascular care patients. Aspirin is also well recognized to reduce fever, pain and inflammation. For use in fever reduction, pain control and inflammation reduction, concentrations will be somewhat higher.

With regard to the vitamins in the compositions of the present invention, this will also depend somewhat on the size, age, gender and health of the patient. Speaking generally, the vitamins will normally be from about 5% to about 1000% of the RDA for that vitamin, most often from about 25% to about 500% of the RDA. Of course, the RDA can vary considerably with the factors illustrated above. Almost any accepted vitamin may be included in the present compositions, for example, vitamins A, D, E, K, C, thiamin, riboflavin, niacin, niacinamide, $B_6$, folate, $B_{12}$, biotin and pantothenic acid can all be included. It is anticipated that the preferred vitamins will include, for example, vitamins A, D, E and C.

In general, the RDA for vitamin A will range from about 2000 International Units (IU) to about 5000 IU. The RDA for vitamin D will range from about 200 IU to about 400 IU. The RDA for vitamin E will range from about 5 IU to about 15 IU. The RDA for vitamin K will range from 5 $\mu$g to 80 $\mu$g. The RDA of vitamin C will range from about 30 mg to about 95 mg. The RDA for thiamin will range from about 0.3 mg to about 1.6 mg. The RDA for riboflavin will range from about 0.4 mg to about 1.8 mg. The RDA for niacin will range from about 5 mg to about 20 mg. The RDA for vitamin $B_6$ will range from about 0.3 mg to about 2.2 mg. The RDA for folate will range from about 25 $\mu$g to about 400 $\mu$g. The RDA for vitamin B-12 will range from about 0.3 $\mu$g to about 2.6 $\mu$g. There are no specific RDA levels for biotin and pantothenic acid. However a safe and adequate range for biotin is from 10 $\mu$g to 100 $\mu$g and an adequate range for pantothenic acid is 2 mg to 7 mg.

Vitamin A precursors (provitamin A, carotenoids) can also be used including β-carotene, α-carotene, cryptoxanthine and the like. The vitamin A esters and β-carotene are highly preferred forms of vitamin A. Vitamin D can be selected from, for example, cholecalciferol (D3), ergocalciferol (D2), and their biologically active metabolites and precursors such as, 1-α-hydroxy vitamin D, 25-hydroxy vitamin D, 1,25-dihydroxy vitamin D and the like. Vitamin D as cholecalciferol is highly preferred. d-α-Tocopherol and its esters are highly preferred as a source for vitamin E. Other sources of vitamin E include β-tocopherol, γ-tocopherol, the tocotrienols and their esters, tocopheryl nicotinate, and the like. Vitamin K can be selected from phylloquinone ($K_1$), menaquinone ($K_2$), menadione and their salts and derivatives. Vitamin $K_1$, is highly preferred. It is noted, however, that vitamin K plays a role in clot formation and is known to interact with oral anticoagulant drugs to decrease their effect. Accordingly, for many utilities, vitamin K will not be used or will be present in low concentrations, as determined by individual patient need.

L-ascorbic acid is particularly preferred for the vitamin supplements of the present invention. However other forms of vitamin C, for example, L-ascorbic acid, D-ascorbic acid, DL-ascorbic acid, D-araboascorbic acid, dehydroascorbic acid, esters of ascorbic acid may also be used. The hydrochloride and nitrate salts of thiamin and thiamin alkyl disulfides such as the prophyidisulfide, tetrahydrofurfuryl disulfide, o-benzoyl disulfide can be used in the present invention. The hydrochloride and nitrate salts are highly preferred. The sources of riboflavin are selected, for example, from crystalline riboflavin coenzyme forms of riboflavin such as flavin adenine dinucleotide, flavin adenine mononucleotide, riboflavin 5'-phosphate and their salts. Riboflavin is highly preferred. For niacin they comprise, for example, nicotinic acid, nicotinamide (niacinamide), the coenzyme forms of niacin such as nicotinamide adenine dinucleotide, and nicotinamide adenine dinucleotide phosphate. Particularly preferred are nicotinamide and nicotinic acid. Vitamin $B_6$ can be selected from hydrochloride salts or 5'-phosphates of pyridoxine, pyridoxamine or pyridoxal. The preferred vitamin $B_6$ is pyridoxine hydrochloride. The folate can be in the form of folic acid, mono and poly-glutamyl folates, dihydro and tetrahydro folates, methyl and formyl folates. Folic acid is a highly preferred form of folate. Sources of vitamin $B_{12}$ are, for example, cyanocobalamin, methylcobalamin, adenosylcobalamin, hydroxocobalamin and the like. Cyanocobalamin is highly preferred. Biotin for use in the vitamin and/or mineral supplements can be selected oxybiotin, biocytin, biotinol and the like. Biotin is highly preferred. For pantothenic acid the sources can be in the form of salts such as calcium pantothenate or as panthenol. Calcium pantothenate is a highly preferred source of pantothenic acid.

The optional mineral supplement component of the compositions of the present invention preferably comprises sources selected from calcium, phosphorus, magnesium, iron, zinc, iodine, selenium, copper, manganese, fluoride, chromium, molybdenum, potassium, and chloride. Additional minerals, though less preferred, include nickel, silicon, boron, tin, vanadium and cobalt. The minerals sources are preferably present in nutritionally relevant amounts, which means that the mineral sources used in the practice of this invention provide a nourishing amount of said minerals. Preferably, this amount comprises at least 5% of the RDA of these minerals, and more preferably, at least 10% of the RDA per unit dose of the finished supplement. Of course, it is recognized that the preferred daily intake of any mineral may vary with the user with greater than the RDA intakes being beneficial in some circumstances.

In general, the RDA for calcium will range from 400 mg for infants to 1200 mg for adults, depending somewhat on age. The RDA for phosphorus ranges from 300 mg to 1200 mg. The RDA for magnesium ranges from 40 mg to 400 mg. The RDA for iron ranges from 6 mg to 30 mg, depending somewhat on age and physiologic state. The RDA for zinc ranges from 5 mg to 19 mg. The RDA for iodine ranges for 40 $\mu$g to 200 $\mu$g. The RDA for selenium ranges from 10 $\mu$to 75 $\mu$g. There are no specific RDA levels for copper, manganese, fluoride, chromium, and molybdenum. However a safe and adequate range for copper is from 0.4 mg to 3.0 mg depending somewhat on age. An adequate range for manganese is 0.3 mg to 5.0 mg per day. A safe and adequate range for fluoride is 0.1 mg to 4.0 mg. A safe and adequate range from chromium is 10 $\mu$g to 200 $\mu$g. A safe and adequate range for molybdenum is 15 $\mu$g to 250 g. There are no specific RDA levels for potassium and chloride, but the estimated minimum requirement of potassium is from 500 to 2000 mg/day for adults and the estimated minimum requirement of chloride is from 180 mg for infants to 750 mg/day for adults.

Specific dietary allowances and estimated safe minimum requirements for nickel, silicon, boron, tin, and vanadium have not been established in humans. However, there is evidence of their function in other mammals and thus, possibly for humans as well. For cobalt, the known nutritional function is as part of cyanocobalamin (vitamin $B_{12}$). The supplement composition comprising use of any of these latter minerals should employ levels known to be safe without risk of toxicity.

The source of the mineral salt, both those with established RDA levels or with safe and adequate intake levels, as well as those with no as yet established human requirement, used in the practice of this invention can be any of the well known salts including carbonate, oxide, hydroxide, chloride, sulfate, phosphate, gluconate, lactate, acetate, fumarate, citrate, malate, amino acids and the like for the cationic minerals and potassium, calcium, magnesium and the like for the anionic minerals. However, the particular salt used and the level will depend upon their interaction with other supplement ingredients.

It will be understood that each of the elements described above, or two or more together, may also find a useful application in other types of applications differing from the type described above. These include, for example, cardiac care, myocardial infarction, transient ischemic attacks, strokes, blood clots, colorectal cancer, migraines, cataracts, immunity, Alzheimer's disease, arthritis, fever, pain, inflammation, pre-eclampsia and eclampsia.

While the invention has been illustrated and described as embodied in a disposable, absorbent article, it is not intended to be limited to the details shown, since it will be understood that various omissions, modifications, substitutions and changes in the forms and details of the formulation illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of this invention.

What is claimed as new and desired to be protected by Letters Patent is set forth in the appended claims:

I claim:

1. A vitamin supplement for the treatment of a cardiac care patient comprising a single composition of:

a) from about 5% to about 1000% of the RDA of vitamins A, D, E, K, C, thiamin, riboflavin, niacin, niacinamide, $B_6$, folate, $B_{12}$, biotin, pantothenic acid and mixtures thereof;

b) from about 10 to 1000 mg acetylsalicylic acid; and c) from about 5% to 500% of the RDA of minerals selected from selenium, zinc, magnesium, calcium, iron, manganese, copper, chromium, cobalt, phosphorous, iodine, potassium, molybdenum, vanadium fluoride, chloride, nickel, tin and silicon.

2. A vitamin supplement as defined in claim 1, further comprising one or more herbal extracts.

3. A vitamin supplement as defined in claim 1, further comprising one or more homeopathic compositions.

4. A vitamin supplement as defined in claim 1, in tablet, capsule, soft-gel capsule, powder, suspension, suppository, sustained release, buffered, liquid effervescent or enteric coated form.

5. The method of treating a cardiac care patient consisting of administering to said patient a vitamin supplement containing a single composition of:

a) from about 5% to about 1000% of the RDA of vitamins A, D, E, K, C, thiamin, riboflavin, niacin, niacinamide, B6, folate, B12, biotin, pantothenic acid and mixtures thereof;

b) from about 10 to 1000 mg acetylsalicylic acid; and c) from about 5% to 500% of the RDA of minerals selected from selenium, zinc, magnesium, calcium, iron, manganese, copper, chromium, cobalt, phosphorous, iodine, potassium, molybdenum, vanadium fluoride, chloride, nickel, tin and silicon.

* * * * *